United States Patent [19]
Grayzel

[11] 3,939,820
[45] Feb. 24, 1976

[54] SINGLE-CHAMBER, MULTI-SECTION BALLOON FOR CARDIAC ASSISTANCE
[75] Inventor: Joseph Grayzel, Englewood, N.J.
[73] Assignee: Datascope Corporation, Paramus, N.J.
[22] Filed: Oct. 29, 1974
[21] Appl. No.: 518,979

[52] U.S. Cl. ................. 128/1 D; 128/344; 417/394
[51] Int. Cl.² .......................................... A61B 19/00
[58] Field of Search ........ 128/1 D, 246, 344, 349 B, 128/349 BV, 214 R; 417/394, 474

[56] References Cited
UNITED STATES PATENTS

| | | | |
|---|---|---|---|
| 2,849,001 | 8/1958 | Oddo | 128/349 B X |
| 3,266,487 | 8/1966 | Watkins et al. | 128/1 D |
| 3,504,662 | 4/1970 | Jones | 128/1 D |
| 3,692,018 | 9/1972 | Goetz et al. | 128/1 D |
| 3,720,200 | 3/1973 | Laird | 128/1 D |

Primary Examiner—Dalton L. Truluck
Attorney, Agent, or Firm—Kenyon & Kenyon Reilly Carr & Chapin

[57] ABSTRACT

A device to be inserted in a blood vessel in order to aid the pumping of blood in only one direction within that vessel which comprises a gas inflatable and deflatable chamber mounted on support means and divided into an occluding section and a pumping section in direct communication with each other, such that it is necessary to deliver gas directly only to the occluding section, thereby enabling the occluding and pumping sections to be mounted on the support means in any order which further enables the device to be inserted from either above or below the vessel and which also permits thinner and therefore more easily insertable support means when the sections are mounted for insertion from below.

4 Claims, 5 Drawing Figures

SINGLE-CHAMBER, MULTI-SECTION BALLOON FOR CARDIAC ASSISTANCE

BACKGROUND OF THE INVENTION

Intra-aortic counterpulsation employing an inflatable balloon within the aorta has become a recognized method for assisting a failing heart and augmenting the flow of blood to the body's various circulatory beds. It has also been shown that uni-directional movement of blood, preferentially to the coronary arteries which nourish the heart muscle itself, is of particular value in aiding the recovery of a failing heart to an adequate and self-sustaining state.

An ordinary, simple, single-chambered balloon was the first type of balloon employed for intra-aortic counterpulsation. However, this simple type of balloon does not insure any degree of preferential flow toward the mouths of the coronary arteries. Rather, it provides omnidirectional flow, i.e., the blood displaced as the balloon inflates will flow toward those vascular beds of lowest resistance. Thus, some blood may flow back within the aorta toward the heart and coronary arteries and some is propelled forward toward the abdomen and lower extremities.

One method of providing uni-directional flow or preferential flow back toward the heart and coronary arteries is disclosed in U.S. Pat. No. 3,692,018. That patent discloses two balloons of different size separated from each other and mounted on a single tubular conduit through which gas is pumped. The tubular conduit passes within both balloons and has holes opening into both balloons so that they may be inflated by the gas pumped through the tube. They are inflated so that the smaller balloon inflates first to occlude the aorta, and the larger balloon second to pump blood away from the occluding balloon. To insure inflation of the occlusive balloon prior to the larger pumping balloon, an obstructing member is placed within the tubular conduit at a point inside the occlusive balloon so that gas first enters the occlusive balloon to inflate it, then flows back into the tubular conduit through holes on the other side of the obstructing member, and continues within the tubular conduit until it reaches holes communicating with the larger pumping balloon, which is then inflated.

There are several disadvantages of this device. First, the pattern of gas flow in and out of the tubular conduit through small holes tends to be turbulent flow, thereby requiring more pumping pressure or time to inflate the balloons. Second, the full diameter of the tubular shaft must be maintained along the axis of both balloons in order to convey the gas. This results in a bulky device to insert into the patient's artery since the ballons must be wrapped around a tubular conduit of full diameter. Third, because of the obstructing member, the occlusive balloon must always be placed on the tubular conduit closer to the pump than the pumping balloon since gas must exit from the occlusive balloon back into the tubular shaft beyond the internal obstructing member, in order to reach the pumping balloon. Because of this order of the two balloons along the tubular shaft, the device can only be used when it is to be inserted into the aorta from the lower portion of the human body, e.g., via the femoral artery in the thigh, so that the pumping balloon lies closer to the heart and the occlusive balloon more distal. This same device cannot be employed for preferential pumping toward the heart and coronary arteries when the operator desires to insert a device from above, as via the brachial or axillary artery, since the device would come to reside in the aorta with the two balloons in the opposite direction or sequence from that required for preferential coronary blood flow, i.e., toward the heart.

SUMMARY OF THE INVENTION

The present invention is a device for cardiac assistance consisting of a single balloon so constructed as to provide preferential or uni-directional pumping without the disadvantages discussed above. The single balloon is constructed so that two sections exist which are only partially separated from each other. Gas enters only one of these sections forcing this section to expand first and occlude the aorta. Then gas entering the first section flows into the second section directly, without any need to re-enter a tubular conduit. The second section is thereby inflated, displacing or pumping blood in one direction only.

Because the pumping section of the balloon fills directly from the occlusive section, no obstructing member is required and the order of the sections in relation to the pump may be selected in accordance with the desired direction of preferential flow and the route of entry to the aorta. Further, holes in the conduit are required only in the occlusive section thereby producing less turbulent flow and requiring less pumping pressure and time to inflate the balloon. Another advantage accrues when the desired order of the occlusive and pumping sections calls for the occlusive section to be closer to the pump and the pumping section just further beyond. In this case, the tubular conduit for gas delivery need only reach the first section, the occlusive section which is to be blown up first and from which the pumping section will be filled with gas. Thus, the full diameter of the tubular conduit need not be maintained within either section of the balloon. Only a thin, supportive member need reside within the balloon sections, thereby enabling a much smaller diameter of the device when the balloon is initially wrapped snugly around the conduit for insertion into the patient's artery. These and other advantages will be apparent from the following description and drawings wherein:

DESCRIPTION OF THE INVENTION

Figure 1:
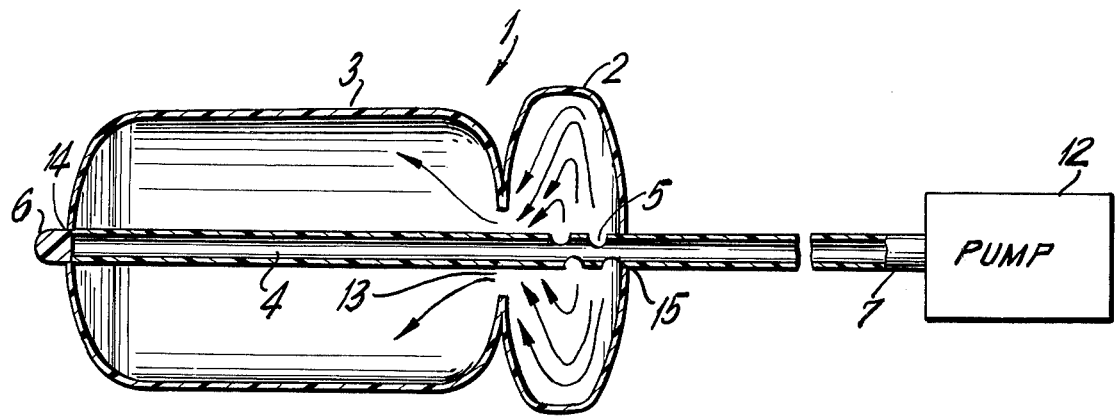
FIG. 1 is a longitudinal, mid-line sectional view of one embodiment of the present invention.
Figure 4:
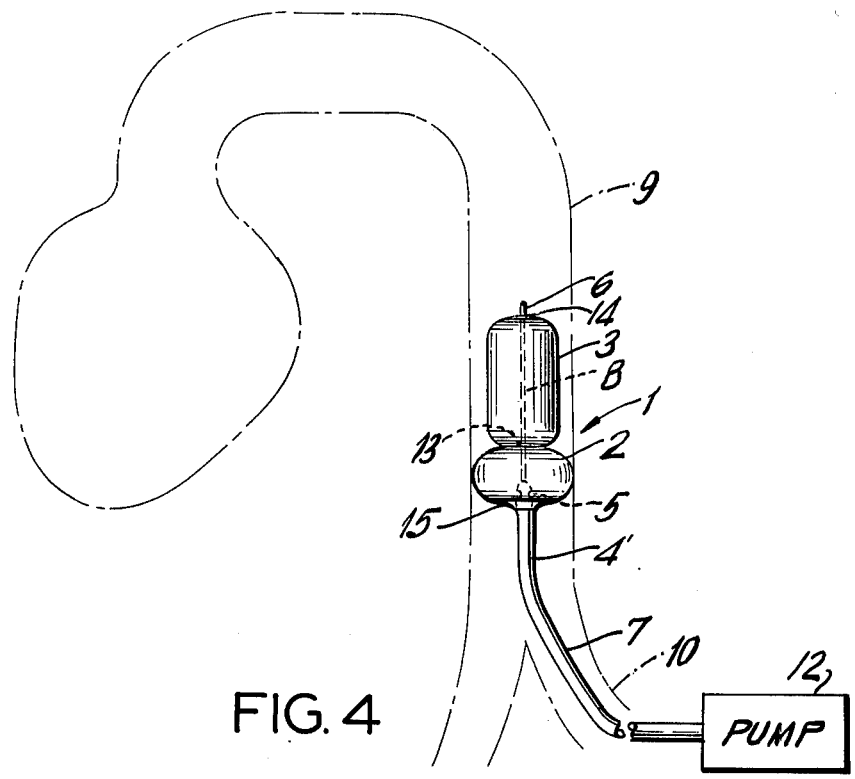
FIG. 4 is a longitudinal, mid-line sectional view of one embodiment of the present invention inserted into the descending aorta from below.
Figure 5:
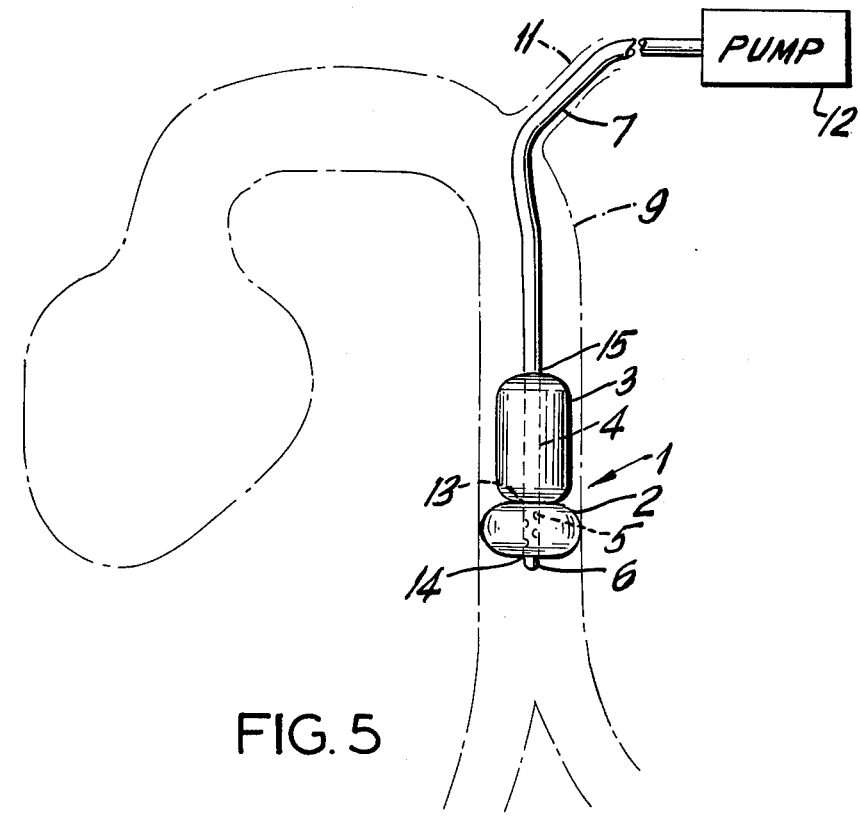
FIG. 5 is a longitudinal, mid-line sectional view of one embodiment of the present invention inserted into the descending aorta from above.

Referring to the figures, where like numerals designate like parts, FIG. 1 shows a balloon member generally designated 1 which is divided into occluding section 2 and pumping section 3. The occluding section 2 and pumping section 3 are not isolated from each other but rather communicate with each other through opening 13. Opening 13 is formed by fabricating balloon 1, as shown, so that the bottom of occluding section 2 and the top of pumping section 3 "neck" down to form opening 13. Occluding section 2 is of larger cross sectional area than pumping section 3 so that when placed within the aorta and inflated, as shown in FIGS. 4 and 5, occluding section 2 will inflate to such a diameter as to substantially block the flow of blood through the aorta, while pumping section 3 will expand enough to increase the pressure within the aorta and thereby aid in pumping the blood, but not enough to fill the aorta and thereby stop the flow as does occluding section 2. It has been found that if occluding section 2 is made substantially spherical and pumping section 3 substantially cylindrical, the above result will be accomplished although other shapes are possible. Balloon 1, as described, is mounted on hollow tube 4 and secured thereto at end points 14 and 15 by any convenient means. Tube 4 has a member 6 at the end thereof to facilitate insertion into the blood vessel. At the opposite end of member 6, tube 4 is attached to line 7 which in turn is connected to pneumatic pump 12. Within occluding section 2 only, tube 4 contains holes 5 which permit gas from pump 12 to enter occluding section 2. When the device is to be inserted into the patient, balloon member 1 in its deflated condition is tightly wrapped around tube 4 and inserted as hereinafter described.

In all devices of this type known today, the device is inserted from below, for example, through the femoral artery. This is because, as explained earlier, the construction of present day devices does not permit the occlusive balloon to be placed further from the pump than the pumping balloon. Also, even when inserted from below through the femoral artery, present day devices require the gas delivery tube to maintain its full thickness to obtain proper gas delivery to both sections. However, this makes insertion difficult because of the overall thickness of the device. The present invention solves both these problems in the following manner.

Figure 2:
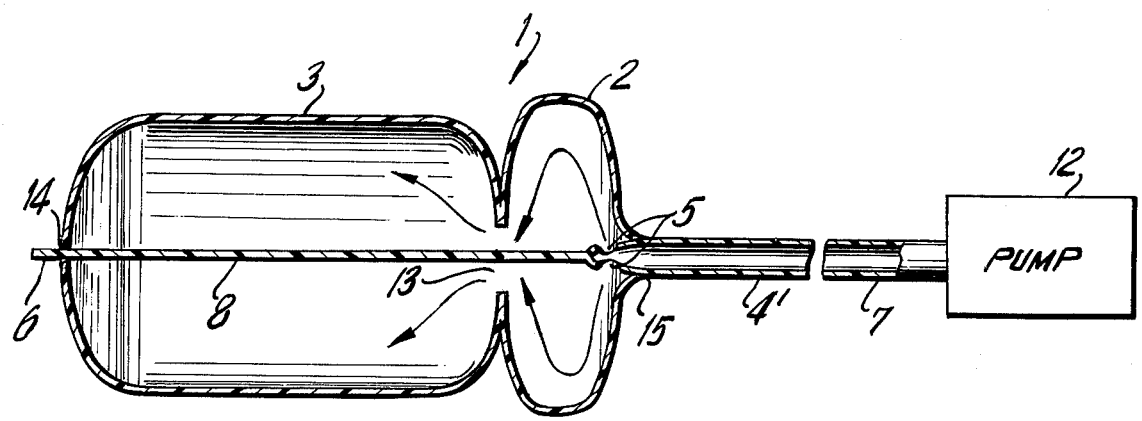
FIG. 2 is a longitudinal, mid-line sectional view of a variation of the embodiment of the present invention shown in FIG. 1.

The gas delivered to the balloon of the present invention is delivered directly only to occluding section 2, where after inflating occluding 2 it flows through opening 13 to pumping section 3. It need not re-enter tube 4 in order to reach pumping section 3. Thus, as shown in FIG. 2, in the case where the device is to be inserted from below, as in the prior art, through the femoral artery, there is no need to have tube 4 run the entire length of the balloon. Rather, tube 4' need only slightly enter occluding section 2 where its holes 5 can deliver the gas. Thereafter all that is needed is a very thin support member 8 to support the balance of the structure. Thus, since the device can be made very much thinner, its insertion in the patient is facilitated reducing the severity of the surgery needed for its insertion. Such a device inserted in the aorta is illustrated in FIG. 4. As can be seen, the device is inserted through femoral artery 10 into the descending aorta 9 where it is lodged and connected to pump 12 through line 7. Line 7 is in turn connected to tube 4' which just enters occluding section 2 and terminates having holes 5 in the end thereof. Connected to tube 4' is thin support member 8 which supports the balance of occluding section 2 and pumping section 3. Support section 8 terminates in member 6 which guided the insertion of the device into the aorta. In operation, pump 12 pumps gas through line 7, into tube 4' out of holes 5 and into occluding section 2. Because of the geometric relationship of occluding section 2 to pumping section 3, most of the gas goes to fill occluding section 2 before passing through opening 13 to pumping section 3. Although some gas may leak into pumping section 3, it is not sufficient to cause pumping. Only when occluding section 2 has substantially completely filled with gas, thus occluding the aorta, does sufficient gas pass through opening 13 into pumping section 3 to cause section 3 to expand and pump blood away from the occlusion toward the heart.

Figure 3:
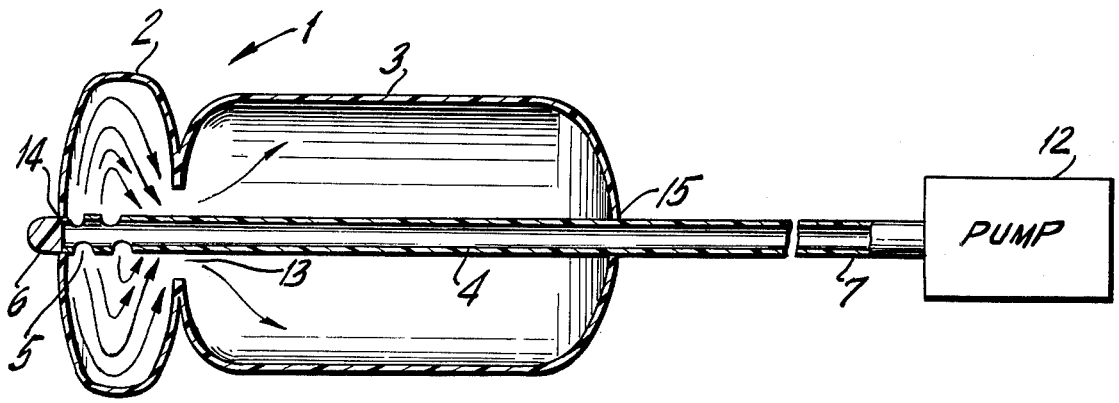
FIG. 3 is a longitudinal, mid-line sectional view of a second embodiment of the present invention.

The fact that gas need only directly enter the occluding section, also makes it possible to construct the device so that, if desired, it may be inserted from above as, for instance, through the axillary artery. This may be required or desirable because of the physical condition of the patient but, as explained earlier, has heretofore been impossible with the prior art devices. Such an embodiment is illustrated in FIG. 3 and as inserted in a patient in FIG. 5. As illustrated in FIG. 5, the device is inserted through axillary artery 11 into aorta 9 where it is lodged and connected to pump 12 through line 7. Line 7 is in turn connected to tube 4 which passes through pumping section 3 and occluding section 2. Tube 4 has holes 5 in the end thereof to permit gas to enter occluding section 2 as previously described. It will be noted that in this embodiment tube 4 must run the entire length of balloon 1 in order to enable the gas to reach occluding section 2. However, unlike the prior art devices, the occluding section 2 does not have to be closer to pump 12 than pumping section 3 thus allowing insertion from above as described.

It can also be seen that in both embodiments, it is only necessary to have holes 5 in tube 4 within occluding section 2, not within the pumping section 3. This provides less turbulent gas flow than occurs with more holes which in turn requires less pumping pressure and less time to inflate the balloon than if tube 4 contained holes in pumping section 3 as well.

Thus, it can be seen that the present invention can be used in a manner not possible with devices of the prior art, i.e., inserted from above, and that even when used in a manner similar to the prior art devices, i.e., inserted from below, it provides the added advantage of utilizing a much thinner support member facilitating insertion and simplifying the surgery required and in both cases it provides for less turbulent and more efficient gas delivery.

What is claimed is:

1. A device to be inserted within a blood vessel for assisting unidirectional blood flow within said vessel comprising:
    a. an inflatable and deflatable chamber mounted upon support means within said chamber, said chamber being divided into an occluding section and a pumping section, said sections being secured to said support means only at their non-adjacent ends, their adjacent ends being only partially separated from each other, not secured to said support means, and thus in direct communication with each other;
    b. gas delivery means terminating only in said occluding section; and
    c. gas providing means connected to said gas delivery means such that gas passes from said providing means to said delivery means and from said delivery means into said occluding section and then from said occluding section directly to said pumping section so as to inflate said occluding section and said pumping section in that order causing said pumping section to pump blood in a direction away from said occluding section.

2. The device of claim 1 wherein said occluding section is distal from and said pumping section is proximate to said gas providing means and a single hollow tube having holes only in the portion thereof within said occluding section constitutes said support means and said gas delivery means.

3. The device of claim 1 wherein said occluding section is proximate to and said pumping section is distal from said gas providing means, and a hollow tube extending only into said occluding section and having holes only in the portion thereof within said occluding section constitutes said gas delivery means and part of said support means, and a rod substantially thinner than said hollow tube and attached to the end thereof which contains said holes constitutes the balance of said support means.

4. The device of claim 1 wherein said occluding section is proximate to and said pumping section is distal from said gas providing means, and a single hollow tube having holes only in the portion thereof within said occluding section constitutes said support means and said gas delivery means.

* * * * *